US011859251B1

(12) United States Patent
Schutz et al.

(10) Patent No.: US 11,859,251 B1
(45) Date of Patent: *Jan. 2, 2024

(54) IDENTIFACTION OF CANCER BIOMARKERS BY ALIGNMENT OF NUCLEIC ACID SEQUENCES

(71) Applicant: Chronix Biomedical, San Jose, CA (US)

(72) Inventors: Ekkehard Schutz, Gottingen (DE); Julia Beck, Gottingen (DE); Howard Urnovitz, San Jose, CA (US)

(73) Assignee: CHRONIX BIOMEDICAL, San Jose, CA (US)

( * ) Notice: Subject to any disclaimer, the term of this patent is extended or adjusted under 35 U.S.C. 154(b) by 997 days.

This patent is subject to a terminal disclaimer.

(21) Appl. No.: 16/459,049

(22) Filed: Jul. 1, 2019

Related U.S. Application Data

(60) Continuation of application No. 15/339,667, filed on Oct. 31, 2016, now Pat. No. 10,378,064, which is a division of application No. 13/088,551, filed on Apr. 18, 2011, now abandoned.

(60) Provisional application No. 61/324,890, filed on Apr. 16, 2010.

(51) Int. Cl.
C12Q 1/6886 (2018.01)
G16B 5/00 (2019.01)

(52) U.S. Cl.
CPC ............. *C12Q 1/6886* (2013.01); *G16B 5/00* (2019.02); *C12Q 2600/112* (2013.01)

(58) Field of Classification Search
None
See application file for complete search history.

(56) References Cited

U.S. PATENT DOCUMENTS

| 6,363,399 | B1 * | 3/2002 | Maslyn ................ G16B 30/10 |
| 2007/0048742 | A1 | 3/2007 | Kang et al. |
| 2009/0127589 | A1 | 5/2009 | Rothberg et al. |
| 2009/0299640 | A1 | 12/2009 | Ellis et al. |
| 2010/0035252 | A1 | 2/2010 | Rothberg et al. |

FOREIGN PATENT DOCUMENTS

WO  WO 2009/051842  4/2009

OTHER PUBLICATIONS

Salani, Ritu, et al. "Measurement of cyclin E genomic copy number and strand length in cell-free DNA distinguish malignant versus benign effusions." Clinical cancer research 13.19 (2007): 5805-5809.*
Ardell, "SCAN MS: adjusting for multiple comparisons in sliding window neutrality tests," Bioinformatics, vol. 2004.
Beck, "Profile of the Circulating DNA in Apparently Healthy Individuals," Clinical Chemistry, vol. 55, p. 730-738, published online Jan. 30, 2009.
Beck et al., "Next Generation Sequencing of Serum Circulating Nucleic Acids from Patients with Invasive Ductal Breast Cancer Reveals Differences to Healthy and Nonmalignant controls," Molecular Cancer Research, 2010, vol. 8, No. 3, pp. 335-342.
Chen, "Characterization of microRNAs in serum: a novel class of biomarkers for diagnosis of cancer and other diseases," Cell Research, vol. 18, p. 997-1006, 2008.
Clarke et al., "Continuous base identification for single-molecule nanopore DNA sequencing," Nature Nanotechnology, Apr. 2009, vol. 4, pp. 265-270.
Di et al., "Peripheral Blood Mutated p53DNA and Its Clinical Value in Human Breast Cancer," Chinese Journal of Oncology, 2003, vol. 25, No. 2, pp. 137-140, with English abstract.
Fleischhacker et al., "Circulating nucleic acids (CNAs) and cancer—A survey," Reviews on Cancer, 2006, vol. 1775, No. 1, p. 181-232.
Goncalves, "Protein Profiling of Breast Tumor Cells and Subtypes," Molecular & Cellular Proteomics, vol. 7, p. 1420-1433, 2008.
Lanza, "mRNA/microRNA gene expression profile in microsatellite unstable colorectal cancer," Molecular Cancer, vol. 6, No. 54, 11 pages, 2007.
Priness, "Evaluation of gene-expression clustering via mutual information distance measure," BMC Bioinformatics, vol. 8, No. 111, 12 pages, 2007.
Silva et al., "Tumor DNA in Plasma at Diagnosis of Breast Cancer Patients Is a Valuable Predictor of Disease-free Survival," Clinical Cancer Research, 2002, vol. 8, No. 12, pp. 3761-3766.
Tong et al., "Diagnostic developments involving cell-free (circulating) nucleic acids," Clinica Chimica Acta, 2006, vol. 363, pp. 187-196.
Umetani et al., "Prediction of Breast Tumor Progression by Integrity of Free Circulating DNA in Serum," Journal of Clinical Oncology, 2006, vol. 24, No. 26, pp. 4270-4276.

(Continued)

*Primary Examiner* — G. Steven Vanni
(74) *Attorney, Agent, or Firm* — KNOBBE, MARTENS, OLSON & BEAR LLP

(57) ABSTRACT

CNA biomarkers can include nucleic acid sequences that are present in circulating nucleic acids obtained from circulatory systems of a population known to have cancer, but that are rarely present, if at all, in circulating nucleic acids obtained from circulatory systems of a control population. Information is received describing one or more sequences obtained from circulating nucleic acids in a population known to have cancer. Information is also received describing one or more sequences obtained from circulating nucleic acids in a control population. A cluster analysis within a predetermined portion of a genome uses the one or more sequences in the circulating nucleic acids obtained from the population known to have cancer and the one or more sequences in the circulating nucleic acids obtained from the control population. Information is generated identifying one or more biomarkers for the cancer based on a cluster search within results of the cluster analysis.

13 Claims, 6 Drawing Sheets

(56) References Cited

OTHER PUBLICATIONS

Van der Vaart, et al., "A Method for Characterization of Total Circulating DNA," Ann. N.Y. Acad. Sci., 2008, vol. 1137, pp. 92-97.
Wilting, "Integrated Genomic and Transcriptional Profiling Identifies Chromosomal Loci with Altered Gene Expression in Cervical Cancer," Genes, Chromosomes & Cancer, vol. 47, p. 890-905, 2008.
Wu et al., "Cell-free DNA: measurement in various carcinomas and establishment of normal reference range," Clinica Chimica Acta, 2002, vol. 321, pp. 77-87.
Yi, "Coupled analysis of gene expression and chromosomal location," Genomics, vol. 85, p. 401-412, 2005.

* cited by examiner

IDENTIFACTION OF CANCER BIOMARKERS BY ALIGNMENT OF NUCLEIC ACID SEQUENCES

CROSS-REFERENCE TO RELATED APPLICATIONS

This Application is a continuation of U.S. patent application Ser. No. 15/339,667, filed on Oct. 31, 2016, which is a divisional of U.S. patent application Ser. No. 13/088,551, filed on Apr. 18, 2011, which claims the benefit of and priority to U.S. Provisional Patent Application No. 61/324,890, filed Apr. 16, 2010 and entitled "ANALYSIS OF CIRCULATING NUCLEIC ACIDS," the subject matter of each of which is hereby incorporated by reference for all purposes.

Tables 1-7 are hereby incorporated by reference for all purposes.

BACKGROUND

The signs of cancer can vary based on the type and location. Common tests to detect cancer include, a biopsy of a tumor, blood chemistries, bone marrow biopsy (for lymphoma or leukemia), chest x-rays, CT scans, MRIs, and other radiography, or the like. Most cancers can be diagnosed by biopsy. Depending on the location of a tumor, the biopsy may be a simple procedure or a serious operation. Many patients with cancer can have CT scans to determine the exact location and size of a tumor or tumors. However, there is a need for less invasive and expensive detection methods that are can also be used effectively and economically.

Accordingly, what is desired is to solve problems relating to detecting cancers in subjects, some of which may be discussed herein. Additionally, what is desired is to reduce drawbacks related to cancer detection methods, some of which may be discussed herein.

BRIEF SUMMARY

The following portion of this disclosure presents a simplified summary of one or more innovations, embodiments, and/or examples found within this disclosure for at least the purpose of providing a basic understanding of the subject matter. This summary does not attempt to provide an extensive overview of any particular embodiment or example. Additionally, this summary is not intended to identify key/critical elements of an embodiment or example or to delineate the scope of the subject matter of this disclosure. Accordingly, one purpose of this summary may be present some innovations, embodiments, and/or examples found within this disclosure in a simplified form as a prelude to a more detailed description presented later.

In various embodiments, methods, processes, systems, non-transitory computer readable medium storing program code, and various apparatus means are provided for the discovery of circulating nucleic acids (CNA) biomarkers associated with cancer. The CNA biomarkers can include nucleic acid sequences that are present in circulating nucleic acids obtained from circulatory systems (e.g., in a serum or plasma sample) of a population known to have cancer, but that are rarely present, if at all, in circulating nucleic acids obtained from circulatory systems (e.g., in a serum or plasma sample) of a normal individual or subject in a control population or population that does not have cancer.

In various embodiments, a method for identifying biomarkers that are relevant to a type of cancer may be implemented by or performed by one or more computer systems. Information is received describing one or more nucleic acid sequences associated with the human genome obtained from circulating nucleic acids in a population known to have the type of cancer. Information is received describing one or more sequences associated with the human genome obtained from circulating nucleic acids in a control population. A cluster analysis is then performed within a predetermined portion of the human genome using the one or more nucleic acid sequences associated with the human genome in the circulating nucleic acids obtained from the population known to have the type of cancer and the one or more nucleic acid sequences associated with the human genome in the circulating nucleic acids obtained from the control population. Information can be generated identifying one or more biomarkers for the type of cancer based on a cluster search within results of the cluster analysis.

In some embodiments, a cluster analysis may be performed within the entire genome of an organism. In some embodiments, a cluster analysis may be performed within a filtered portion of the genome. Filtering techniques may include aligning one or more sequences associated with the human genome in circulating nucleic acids obtained from a population known to have a type of cancer and one or more sequences associated with the human genome in the circulating nucleic acids obtained from the control population. A group comparison then may be performed using a non-parametric median test to determine a plurality of chromosomal regions. Each chromosomal region in the plurality of chromosomal regions may be ranked in response to linear multivariate regression modeling and Akaike's information criterion. In one aspect, a predetermined number of the highest ranked chromosomal regions in the plurality of chromosomal regions may be selected as a predetermined portion of the genome within which to perform the cluster analysis and/or search.

In further embodiments, a cluster analysis may include determining the number of subjects in the control population with a hit in each of a plurality of base pair intervals of a predetermined size within the portion of the genome. The cluster analysis may include determining the number of subjects in the population known to have the type of cancer with a hit in each of the plurality of base pair intervals within the portion of the genome. A cluster may be determined within the predetermined portion of the genome that includes a predetermined number of subjects in the population known to have the type of cancer that is greater than a predetermined amount of subjects in the control population. A chromosomal region then may be identified or determined that is associated with the cluster.

In some aspects, determining a cluster within the predetermined portion of the human genome that includes a predetermined number of subjects in the population known to have the type of cancer that is greater than a predetermined amount of subjects in the control population may include determining one or more clusters of cancer samples without any control samples within at least a predefined or predetermined number of base pairs. In further aspects, determining a cluster within the predetermined portion of the human genome that includes a predetermined number of subjects in the population known to have the type of cancer that is greater than a predetermined amount of subjects in the control population may include determining one or more clusters of cancer samples with no more than one control sample within at least a predefined or predetermined number base pairs.

In some embodiments, generating information identifying one or more biomarkers in the circulating nucleic acids in the population known to have the type of cancer based on a cluster search within results of the cluster analysis may include generating information identifying one or more biomarkers relevant to breast cancer, lung cancer, prostate cancer, or colorectal cancer.

In further embodiments, non-transitory computer-readable media are provided storing program code for identifying biomarkers that are relevant to a type of cancer. The computer readable media may include code for receiving information describing one or more nucleic acid sequences associated with the human genome obtained from circulating nucleic acids in a population known to have the type of cancer, code for receiving information describing one or more sequences associated with the human genome obtained from circulating nucleic acids in a control population, code for performing a cluster analysis within a predetermined portion of the human genome using the one or more nucleic acid sequences associated with the human genome in the circulating nucleic acids obtained from the population known to have the type of cancer and the one or more nucleic acid sequences associated with the human genome in the circulating nucleic acids obtained from the control population, and code for generating information identifying one or more biomarkers for the type of cancer based on a cluster search within results of the cluster analysis.

In still further embodiments, apparatuses and systems for identifying biomarkers that are relevant to a type of cancer may include various means, such as a processor and a memory in communication with the processor and configured to store program code. The program code may be configured to configured the processor to receive information describing one or more nucleic acid sequences associated with the human genome obtained from circulating nucleic acids in a population known to have the type of cancer, receive information describing one or more sequences associated with the human genome obtained from circulating nucleic acids in a control population, perform a cluster analysis within a predetermined portion of the human genome using the one or more nucleic acid sequences associated with the human genome in the circulating nucleic acids obtained from the population known to have the type of cancer and the one or more nucleic acid sequences associated with the human genome in the circulating nucleic acids obtained from the control population, and generate information identifying one or more biomarkers for the type of cancer based on a cluster search within results of the cluster analysis.

Accordingly, CNA biomarkers for various cancers can be identified to include nucleic acid sequences that are present in circulating nucleic acids obtained from circulatory systems of a population known to have cancer, but that are rarely present, if at all, in circulating nucleic acids obtained from circulatory systems of a control population.

A further understanding of the nature of and equivalents to the subject matter of this disclosure (as well as any inherent or express advantages and improvements provided) should be realized in addition to the above section by reference to the remaining portions of this disclosure, any accompanying drawings, and the claims.

BRIEF DESCRIPTION OF THE DRAWINGS

In order to reasonably describe and illustrate those innovations, embodiments, and/or examples found within this disclosure, reference may be made to one or more accompanying drawings. The additional details or examples used to describe the one or more accompanying drawings should not be considered as limitations to the scope of any of the claimed inventions, any of the presently described embodiments and/or examples, or the presently understood best mode of any innovations presented within this disclosure.

DETAILED DESCRIPTION

Figure 1:
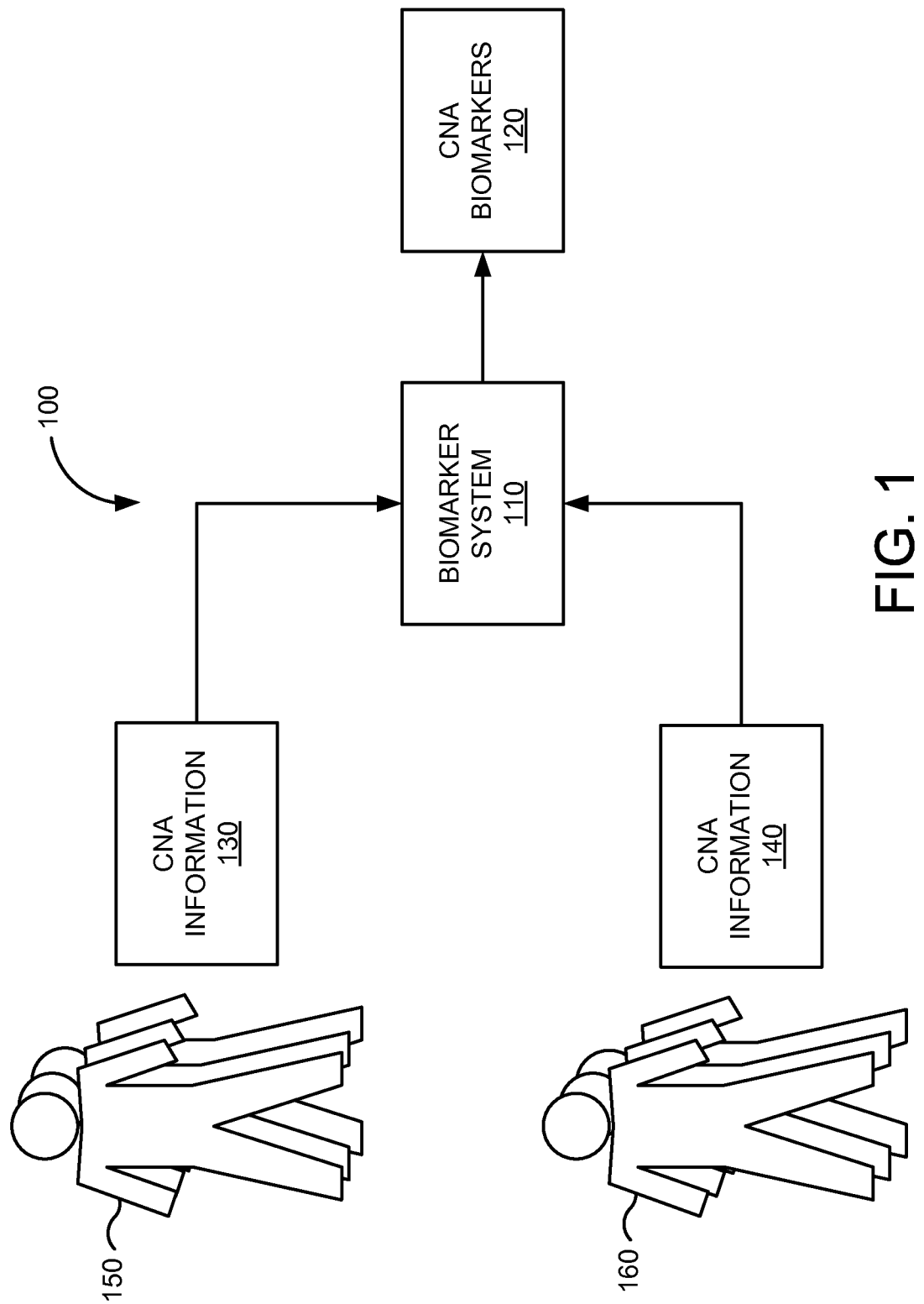
FIG. 1 is a simplified illustration of a system that may be used in an embodiment of the present invention to determine biomarkers relevant to a given cancer or particular type of cancer from circulating nucleic acids.

In various embodiments, methods, processes, systems, non-transitory computer readable medium storing program code, and various apparatus means are provided for the discovery of circulating nucleic acids (CNA) biomarkers associated with cancer. The CNA biomarkers can include nucleic acid sequences that are present in circulating nucleic acids obtained from circulatory systems (e.g., in a serum or plasma sample) of a population known to have cancer, but that are rarely present, if at all, in circulating nucleic acids obtained from circulatory systems (e.g., in a serum or plasma sample) of a normal individual or subject in a control population or population that does not have cancer.

In order to better understand one or more of the inventions presented within this disclosure, various terms, phrases, and aspects of at least one environment within which various embodiments may operate will first be described.

As used herein, "circulating nucleic acids" (CNAs) refers to acellular nucleic acids that are present in a circulatory system of an organism (e.g., in the blood or lymph).

As used herein, a "biomarker" refers to a nucleic acid sequence that corresponds to a chromosomal region of a chromosome associated with a genome of a particular organism (e.g., the human genome). Thus, CNA biomarkers can include nucleic acid sequences that are present in circulating nucleic acids obtained from circulatory systems (e.g., in a serum or plasma sample) of a population known to have cancer, but that are rarely present, if at all, in circulating nucleic acids obtained from circulatory systems (e.g., in a serum or plasma sample) of a normal individual or subject in a control population or population that does not have cancer.

As used herein, a "chromosomal region" refers to a part of a chromosome defined either by anatomical details, linkage groups, or by a predetermined base pair interval. In one aspect related to CNA biomarkers for breast cancer, a chromosomal region listed in anyone of Tables 1 to 6 refers to the region of the chromosome that corresponds to the nucleotide positions indicated in the Table. As understood in the art, there are naturally occurring polymorphisms in the genome of individuals. Thus, each chromosome regions listed in the table encompasses allelic variants as well as a particular sequence in a database, (e.g., the sequences in the Table of Sequence appended hereto that correspond to the chromosomal regions noted). An allelic variant typically has at least 95% identity, often at least 96%, at least 97%, at least 98%, or at least 99% identity to the sequence of a chromosomal region noted in the Tables that is present in a particular database, (e.g., Homo sapiens Build 37.1 provided by the National Center for Biotechnology Information and found at http://www.ncbi.nlm.nih.gov/mapview/).

As used herein, "detecting a biomarker" refers to detecting a nucleic acid sequence from a chromosomal region identified to be relevant to a given cancer or particular type of cancer. In one aspect relevant to breast cancer, detecting a biomarker may refer to detecting a nucleic acid sequence from a chromosomal region listed in any of Tables 2-6. A biomarker is considered to be present if any nucleic acid sequence present in the CNA is unambiguously assigned to the chromosomal region.

As used herein, "unambiguously assigned" refers to determining that a DNA detected in the CNA of an individual or subject is from a particular chromosomal region. Thus, in detection methods that employ hybridization, a probe can hybridize specifically to that region. In detection methods that employ sequencing, the sequence can be assigned to that region based on well-known algorithms for identity, such as the BLAST algorithm using high stringent parameters, such as e<0.0001. In another aspect, such a sequence cannot have a further equally fitting hit on the used database.

As used herein, "hybridization" refers to the formation of a duplex structure by two single stranded nucleic acids due to complementary base pairing. Hybridization can occur between exactly complementary nucleic acid strands or between nucleic acid strands that contain minor regions of mismatch.

As used herein, "substantially complementary" refers to sequences that are complementary except for minor regions of mismatch. Typically, the total number of mismatched nucleotides over a hybridizing region is not more than 3 nucleotides for sequences about 15 nucleotides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. For example, computer software for calculating duplex stability is commercially available from MeltCalc (Gottingen Germany); e.g. MeltCalc version 2, or National Biosciences, Inc. (Plymouth, Minn.); e.g., OLIGO version 5, or from DNA Software (Ann Arbor, Michigan), e.g., Visual OMP 6.

Stringent, sequence-specific hybridization conditions, under which an oligonucleotide will hybridize only to the exactly complementary target sequence, are well known in the art (see, e.g., the general references provided in the section on detecting polymorphisms in nucleic acid sequences). Stringent conditions are sequence-dependent and will be different in different circumstances. Generally, stringent conditions are selected to be from about 5° C. lower to 5° C. higher than the thermal melting point (Tm) for the specific sequence at a defined concentration, ionic strength, and pH. The Tm is the temperature (under defined concentration, ionic strength, and pH) at which 50% of the double stranded DNA molecules have dissociated and the free Gibbs energy is substantially or at zero. Relaxing the stringency of the hybridizing conditions will allow sequence mismatches to be tolerated; the degree of mismatch tolerated can be controlled by suitable adjustment of the hybridization conditions.

As used herein, "primer" refers to an oligonucleotide that acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer includes a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5' end of the primer that hybridizes to a capture oligonucleotide.

As used herein, "probe" refers to an oligonucleotide that selectively hybridizes to a target nucleic acid under suitable conditions. A probe for detection of biomarker sequences identified as described herein to be relevant to a given cancer or particular type of cancer can be any length, e.g., from 15-500 bp in length. Typically, in probe-based assays, hybridization probes that are less than 50 bp are preferred.

As used herein, "target sequence" or "target region" refers to a region of a nucleic acid that is to be analyzed and comprises the polymorphic site of interest.

As used herein, "nucleic acid," "polynucleotide" and "oligonucleotide" refer to primers, probes, and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA. Oligonucleotides for use in the invention may be used as primers and/or probes.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, N6-methyladenine, N6-tert-butyl-benzyl-adenine, imidazole, substituted imidazoles, 5-fluorouracil, 5 bromouracil, 5-chlorouracil, 5-iodouracil, hypoxanthine, xanthine, 4-acetylcytosine, 5 (carboxyhydroxymethyl)uracil, 5 carboxymethylaminomethyl-2-thiouridine, 5 carboxymethylaminomethyluracil, dihydrouracil, beta-D-galactosylqueosine, inosine, N 6 isopentenyladenine, I-methylguanine, I-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'methoxycarboxymethyluracil, 5-methoxyuracil, 2-methylthio-N6-isopentenyladenine, uracil-5-oxyacetic acid (v), wybutoxosine, pseudouracil, queosine, 2 thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6- diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785, each of which is incorporated herein by reference in its entirety. Furthermore, a nucleic acid, polynucleotide or oligonucleotide can comprise one or more modified sugar moieties including, but not limited to, arabinose, 2-fluoroarabinose, xylulose, and a hexose.

As used herein, "arrays," "microarrays," and "DNA chips" refer interchangeably to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. The arrays are prepared using known methods.

FIG. 1 is a simplified illustration of system 100 that may be used in an embodiment of the present invention to determine biomarkers relevant to breast cancer from circulating nucleic acids. FIG. 1 is merely illustrative of an embodiment incorporating the present invention and does not limit the scope of the invention as recited in the claims. One of ordinary skill in the art would recognize other variations, modifications, and alternatives.

In one embodiment, system 100 includes biomarker system 110. Biomarker system 110 includes hardware and/or software elements configured for determining biomarkers. Biomarker system 110 can include one or more general purpose computers (including, merely by way of example, personal computers and/or laptop computers running any appropriate flavor of operating systems) and/or workstation and mainframe computers running any of a variety of commercially-available UNIX or UNIX-like operating systems. Biomarker system 110 can also have any of a variety of applications, including one or more applications configured to perform methods of the invention, as well as one or more client and/or server applications, web applications, or the like. Alternatively, biomarker system 110 can be any other electronic device, such as a thin-client computer, Internet-enabled mobile telephone, and/or personal digital assistant, capable of communicating via a network and/or displaying and navigating web pages or other types of electronic documents.

Certain embodiments of biomarker system 100 can operate in a networked environment, which can include one or more communications networks (not shown) that can be any type of network familiar to those skilled in the art that can support data communications using any of a variety of commercially-available protocols, including without limitation TCP/IP, SNA, IPX, AppleTalk, and the like. Merely by way of example, a communications network can be a local area network ("LAN"), including without limitation an Ethernet network, a TokenRing network and/or the like; a wide-area network; a virtual network, including without limitation a virtual private network ("VPN"); the Internet; an intranet; an extranet; a public switched telephone network ("PSTN"); an infra-red network; a wireless network, including without limitation a network operating under any of the IEEE 802.11 suite of protocols, the Bluetooth protocol, and/or any other wireless protocol; and/or any combination of these and/or other networks.

Embodiments of biomarker system 110 can include one or more server computers configured with an operating system including without limitation any of those discussed above, as well as any commercially-available server operating systems. Each server computer may also be running one or more applications, which can be configured to provide services to one or more clients and/or other servers. Merely by way of example, one of the server computers may be a web server, which can be used, merely by way of example, to process requests for web pages or other electronic documents. The web server can also run a variety of server applications, including HTTP servers, FTP servers, CGI servers, database servers, Java servers, and the like. In some embodiments of the invention, the web server may be configured to serve web pages that can be operated within a web browser.

In certain embodiments, biomarker system 110 can include one or more databases (not shown). The location of the databases is discretionary: merely by way of example, a database might reside on a storage medium local to (and/or resident in) a computer associated with biomarker system 110. Alternatively, a database can be remote from any biomarker system 110, so long as it can be in communication (e.g., via a communications network) with biomarker system 110.

In various embodiments, biomarker system 110 can determine CNA biomarkers relevant to one or more cancers or one or more types of cancer. In one aspect, biomarker system 110 determines CNA biomarkers 120 from CNA information 130 and CNA information 140. CNA biomarkers 120 may represent nucleic acid sequences that are present in circulating nucleic acids obtained from circulatory systems (e.g., in a serum or plasma sample) of a population known to have cancer, but that are rarely present, if at all, in circulating nucleic acids obtained from circulatory systems (e.g., in a serum or plasma sample) of a normal individual or subject in a control population or population that does not have cancer.

In various aspects, CNA information 130 includes data representing population 150. Population 150 may include individuals or subjects that have been diagnosed with a given cancer or particular type of cancer and/or are known to have the given cancer or particular type of cancer. Some examples of cancers had by individuals or subjects in population 150 are prostate cancer, lung cancer, colon cancer, breast cancer, gastric cancer, brain cancer, cervical cancer, Hodgkin's lymphoma, non-Hodgkin's lymphoma, kidney cancer, leukemia, liver cancer, ovarian cancer, skin cancer, testicular cancer, thyroid cancer, uterine cancer. CNA information 130 may include information about individuals or subjects within population 150 or population 150 as a while, such as population statistics (e.g., name, age, sex, race, location, etc.) patient and family history, environmental data, lab and diagnostic data, or the like. In one aspect, CNA information 130 includes data representing acellular nucleic acids that are present in the blood or lymph of individuals or subjects in population 150.

In various aspects, CNA information 140 includes data representing population 160. Population 160 may include individuals or subjects that are known not to have the given cancer or particular type of cancer of population 150. CNA information 140 may include information about individuals or subjects within population 160 or population 160 as a while, such as population statistics (e.g., name, age, sex, race, location, etc.) patient and family history, environmental data, lab and diagnostic data, or the like. In one aspect, CNA information 140 includes data representing acellular nucleic acids that are present in the blood or lymph of individuals or subjects in population 160.

Figure 2:
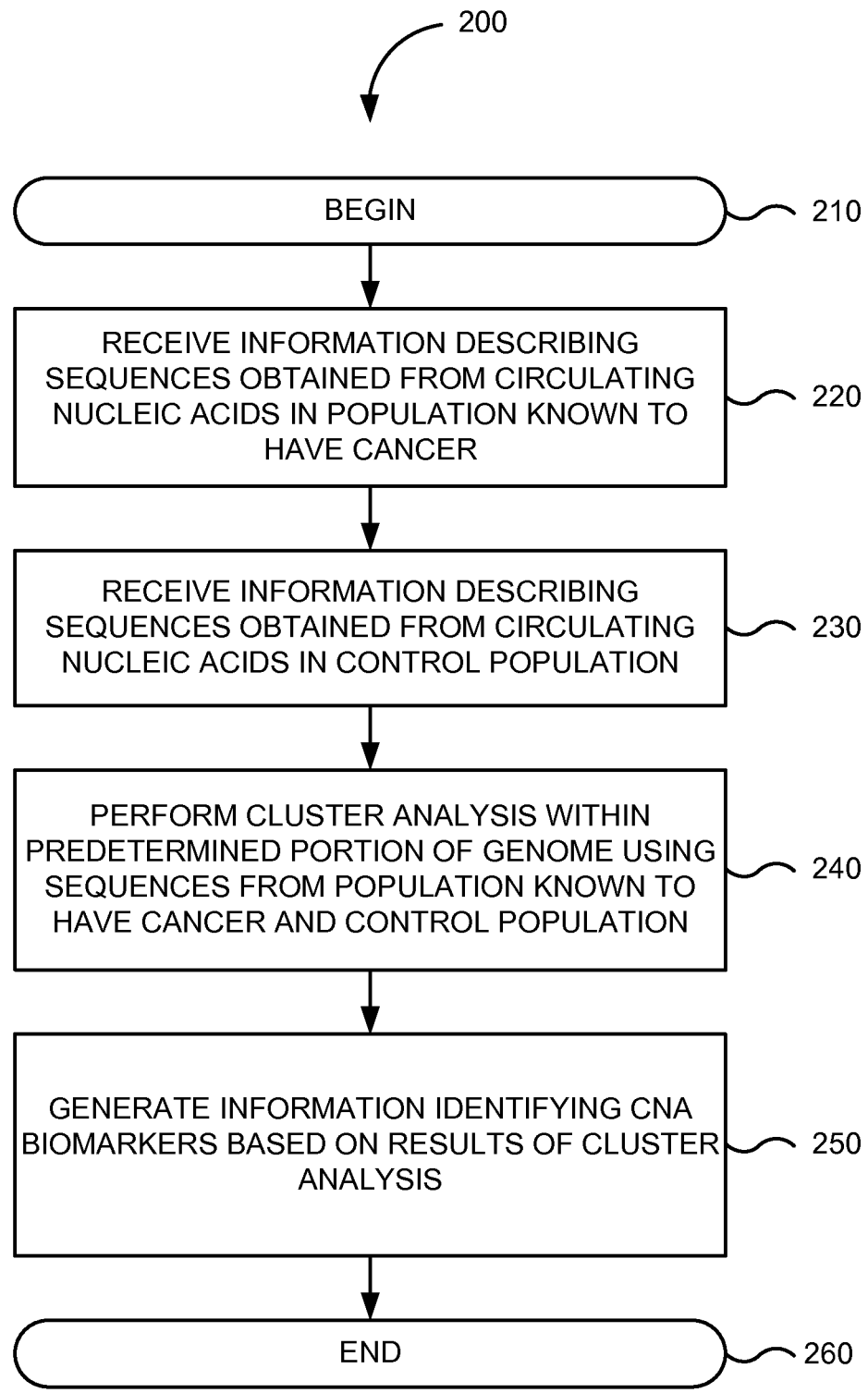
FIG. 2 is a flowchart of a method for determining biomarkers relevant to a given cancer or particular type of cancer from circulating nucleic acids in one embodiment according to the present invention.

FIG. 2 is a flowchart of method 200 for determining biomarkers relevant to a given cancer or particular type of cancer from circulating nucleic acids in one embodiment according to the present invention. Implementations of or processing in method 200 depicted in FIG. 2 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 200 depicted in FIG. 2 begins in step 210.

In step 220, information describing one or more nucleic acid sequences obtained from circulating nucleic acids in a population known to have a given cancer or particular type of cancer is received. For example, biomarker system 110 may receive information stored in a computer readable form obtained from sequencing circulating nucleic acids obtained from individuals or subjects in population 150. Individuals or subjects in population 150 may be known to have any given cancer or type of cancer, such as prostate cancer, lung cancer, colon cancer, breast cancer, gastric cancer, brain cancer, cervical cancer, Hodgkin's lymphoma, non-Hodgkin's lymphoma, kidney cancer, leukemia, liver cancer, ovarian cancer, skin cancer, testicular cancer, thyroid cancer, uterine cancer, or the like. The one or more nucleic acid sequences obtained from circulating nucleic acids may be associated with the human genome or the genome of another organism.

Sequencing may include dideoxy sequencing-based methods, Maxam and Gilbert sequencing, or others that are also known. In some embodiments, circulating nucleic acids obtained from an individual or subject in populations 150 and 160 can be sequenced using a large-scale sequencing method that provides the ability to obtain sequence information from many reads. Such sequencing platforms include those commercialized by Roche 454 Life Sciences, Illumina, and Applied Biosystem's SOLiD systems.

The Roche 454 Life Sciences sequencing platform involves using emulsion PCR and immobilizing DNA fragments onto bead. Incorporation of nucleotides during synthesis is detected by measuring light that is generated when a nucleotide is incorporated.

The Illumina technology involves the attachment of randomly fragmented genomic DNA to a planar, optically transparent surface. Attached DNA fragments are extended and bridge amplified to create an ultra-high density sequencing flow cell with clusters containing copies of the same template. These templates are sequenced using a sequencing-by-synthesis technology that employs reversible terminators with removable fluorescent dyes.

Methods that employ sequencing by hybridization may also be used. Such methods, e.g., used in the ABI SOLiD technology uses a pool of all possible oligonucleotides of a fixed length, labeled according to the sequenced position. Oligonucleotides are annealed and ligated; the preferential ligation by DNA ligase for matching sequences results in a signal informative of the nucleotide at that position. During one ligation, the two unambiguous nucleotides of that said oligonucleotide can be interrogated, e.g., by shifting the ligation start point in several round, where each nucleotide can be detected in duplicate and/or with a high accuracy.

The sequences can be determined using any other DNA sequencing method including, e.g., methods that use semiconductor technology to detect nucleotides that are incorporated into an extended primer by measuring changes in current that occur when a nucleotide is incorporated (see, e.g., U.S. Patent Application Publication Nos. 2009/0127589 and 2010/0035252). Other techniques include direct label-free exonuclease sequencing in which nucleotides cleaved from the nucleic acid are detected by passing through a nanopore (Oxford Nanopore) (Clark et al., Nature Nanotechnology 4: 265-270, 2009); Single Molecule Real Time (SMRT™) DNA sequencing technology (Pacific Biosciences), which is a sequencing-by synthesis technique; or measuring the pH change as result of nucleotide incorporation during synthesis (IonTorrent).

In step 230, information describing one or more nucleic acid sequences obtained from circulating nucleic acids in a control population is received. For example, biomarker system 110 may receive information stored in a computer readable form obtained from sequencing circulating nucleic acids obtained from individuals or subjects in population 160. The sequences can be determined using any of the DNA sequencing methods discussed herein, as well as others.

In step 240, a cluster analysis is performed within a predetermined portion of a genome using the one or more nucleic acid sequences in the circulating nucleic acids obtained from the population known to have a given cancer or particular type of cancer and the one or more nucleic acid sequences in the circulating nucleic acids obtained from the control population. Biomarker system 110 may perform the cluster analysis on the entire human genome or, in some embodiments, a filtered portion of the human genome as the predetermined portion. In one example, biomarker system 110 may perform a cluster analysis to assign each of one or more nucleic acid sequences associated with the human genome in circulating nucleic acids obtained from population 150 and/or 160 into subsets or clusters within base pair intervals, chromosomal regions, or the like, associated with the human genome. Biomarker system 110 may assign each of one or more nucleic acid sequences associated with the human genome in circulating nucleic acids obtained from population 150 and/or 160 into subsets or clusters within the same base pair intervals, chromosomal regions, or the like, associated with the human genome determined from the other population.

In some aspects, biomarker system 110 may determine through the cluster analysis the number of hits within a series of predetermined base pair interval of one or more nucleic acid sequences associated with the human genome in circulating nucleic acids obtained from population 150. Biomarker system 110 may determine the number of hits within the same series of predetermined base pair interval of one or more nucleic acid sequences associated with the human genome in circulating nucleic acids obtained from population 160.

In step 250, information identifying one or more CNA biomarkers is generated based on a cluster search within results of the cluster analysis. The information may include data about nucleic acid sequences that are present in circulating nucleic acids obtained from circulatory systems (e.g., in a serum or plasma sample) of population 150 known to have cancer, but that are rarely present, if at all, in circulating nucleic acids obtained from circulatory systems (e.g., in a serum or plasma sample) of a normal individual or subject in a control population or population 160 that does not have cancer.

In various embodiments, biomarker system 110 may determine biomarkers as nucleic acid sequences in the population known to have a given cancer or particular type of cancer that corresponds to chromosomal regions. These biomarkers may satisfy various criteria evidenced by one or more cluster searches within the results of the cluster analysis. For example, biomarker system 110 may restrict identification of biomarkers to cluster of breast cancer samples having had a distance to the next normal sample hit of at least a predefined or predetermined number of base pairs (e.g., 200 bp). Choosing a predetermined number of these cluster regions can provide an 89% sensitivity with 100% true negative classification, where a sample is called positive if at least one hit is found in any of the cluster regions (see Table 2).

In further embodiments, biomarker system 110 may restrict identification of biomarkers to additional clusters where only one or less normal sample was found in a cluster of at least a predefined or predetermined number of cancer samples (e.g., 12 cancer samples). Choosing a predetermined number of these cluster regions can yield 94% true positives and 95% true negatives. In one example, total length was calculated to be 667 kbp (see Table 3). Use of 323 regions provides an 87% sensitivity and 100% specificity. In other embodiments, biomarker system 110 may restrict identification of biomarkers to chromosomal regions indicated by bold font in Tables 3 and 4 that have been observed to be present infrequently in CNA obtained from normal individuals; however, given the low frequency of occurrence in normal samples relative to the higher frequency of occurrence in breast cancer, the presence of the biomarker in a patient indicates that the patient has a 90% or greater likelihood of having breast cancer. FIG. 2 ends in step 260.

Accordingly, biomarker system 110 can determine CNA biomarkers relevant to one or more cancers or one or more types of cancer. As discussed above, CNA biomarkers 120 may represent nucleic acid sequences that are present in circulating nucleic acids obtained from circulatory systems (e.g., in a serum or plasma sample) of a population known to have cancer, but that are rarely present, if at all, in circulating nucleic acids obtained from circulatory systems (e.g., in a serum or plasma sample) of a normal individual or subject in a control population or population that does not have cancer. Biomarker system 110 may identify CNA biomarkers 120 relevant to a variety of cancer or types of cancers where a sample can be called positive if at least one hit is found in any of the identified cluster regions.

Figure 3:
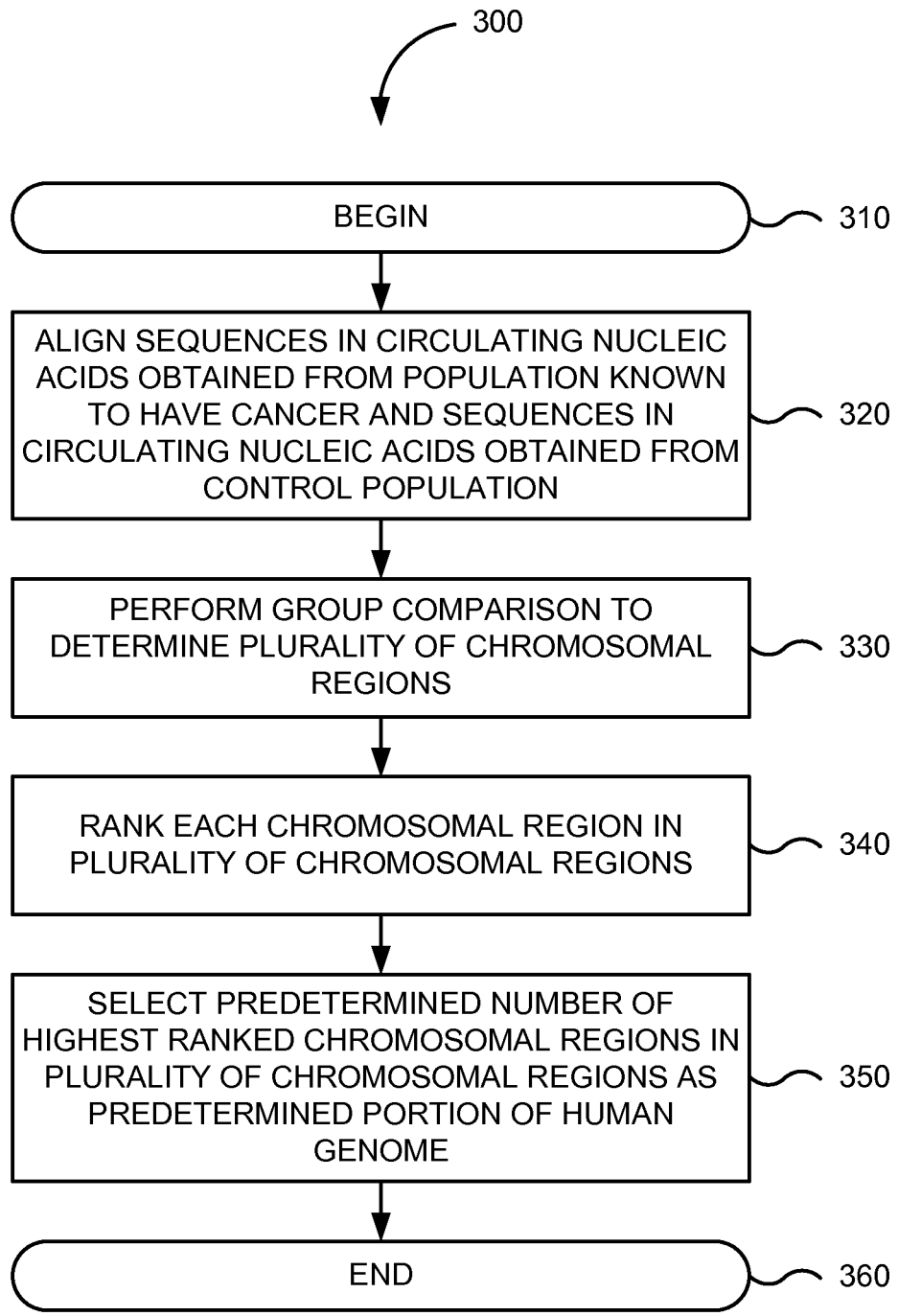
FIG. 3 is a flowchart of a method for filtering circulating nucleic acids in one embodiment according to the present invention.

As discussed above, Biomarker system 110 may perform the cluster analysis on the entire human genome or, in some embodiments, a filtered portion of the human genome as the predetermined portion. FIG. 3 is a flowchart of method 300 for filtering circulating nucleic acids in one embodiment according to the present invention. Implementations of or processing in method 300 depicted in FIG. 3 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 300 depicted in FIG. 3 begins in step 310.

In step 320, one or more nucleic acid sequences in circulating nucleic acids obtained from a population known to have a given cancer or particular type of cancer and one or more nucleic acid sequences in circulating nucleic acids obtained from a control population are aligned. For example, to investigate which sequences are disease associated in human subjects all alignments that can be unambiguously placed on the human genomic database (Homo sapiens Build 37.1 http://www.ncbi.nlm.nih.gov/mapview/) may be used.

In step 330, a group comparison is performed using a non-parametric median test to determine a plurality of chromosomal regions. Biomarker system 110 may categorized the aligned sequences into 4060 region of 750,000 bp intervals. In some embodiments, biomarker system 110 selects for differences between normal controls and cancer patients on the basis of the group comparison using a non-parametric median test. In one example, five hundred chromosomal regions having the lowest p-values may be used for further analyses.

In step 340, each chromosomal region in the plurality of chromosomal regions is ranked in response to linear multivariate regression modeling and Akaike's information criterion. For example, biomarker system 110 may perform linear multivariate regressions modeling using the above selected 750 k regions as independent parameters. In one example, a bootstrap of randomly selected samples for linear multivariate regressions modeling is performed to reduce or otherwise eliminate bias. Biomarker system 110 may calculate the MVRs based on Akaike's Information criterion (AIC) using about 90,000,000 models (2 to 5 parameters). Biomarker system 110 may rank each independent parameter according to the Akaike weight sums. In one embodiment, biomarker system 110 selects the highest ranked 42 as given in Table 1.

In step 350, a predetermined number of the highest ranked chromosomal regions in plurality of chromosomal regions are selected as the predetermined portion of human genome within which to perform the cluster analysis. For example, biomarker system 110 may select the highest ranking thirty two 750 k regions to apply to population 150 known to have cancer and population 160 or normal controls. FIG. 3 ends in step 360.

Accordingly, biomarker system 110 may perform the cluster analysis on a filtered portion of the human genome being those highest ranking thirty two 750 k chromosomal regions selected for differences between normal controls and cancer patients. In various embodiments, in applying the filtered regions to population 150 known to have cancer and population 160 or normal controls, biomarker system 110 may determine performance calculations showing a sensitivity of 79% and a specificity of 97%.

Figure 4:
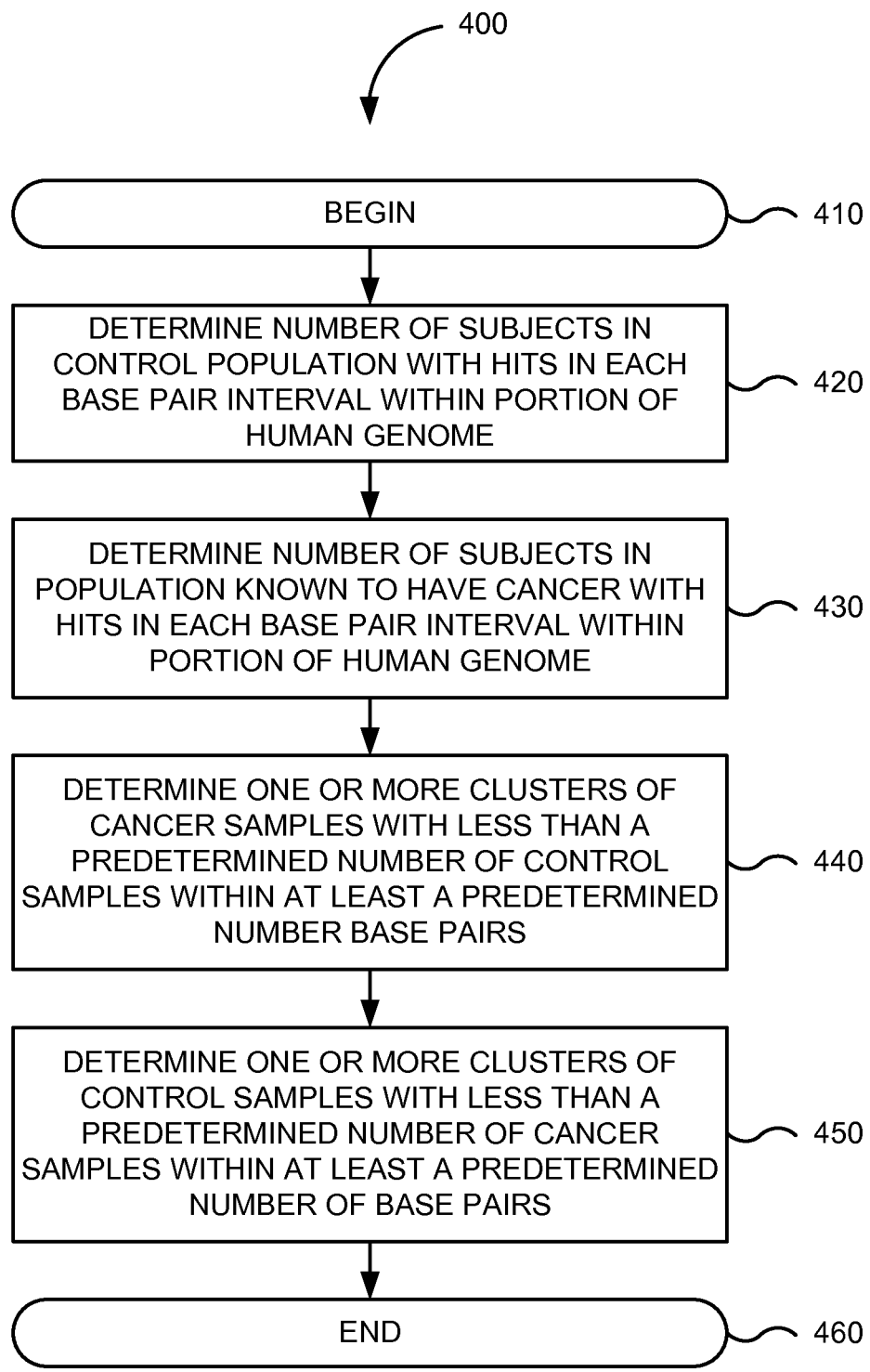
FIG. 4 is a flowchart of a method for determining hot spots in a predetermined portion of the human genome that can identify biomarkers relevant to a given cancer or particular type of cancer in one embodiment according to the present invention.

FIG. 4 is a flowchart of method 400 for determining hot spots in a predetermined portion of the human genome that can identify biomarkers relevant to a given cancer or particular type of cancer in one embodiment according to the present invention. Implementations of or processing in method 400 depicted in FIG. 4 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 400 depicted in FIG. 4 begins in step 410.

In step 420, a number is determined of individuals or subjects in a control population with hits in each base pair interval within a predetermined portion of the human genome. While the human genome is used for the purposes of this illustration, other non-human genomes may be used. In step 430, a number is determined of individuals or subjects in a population known to have a given cancer or particular type of cancer with hits in each base pair interval within the predetermined portion of the human genome.

In step 440, one or more clusters of cancer samples are determined with less than a predetermined number of control samples within at least a predetermined number of base pairs. For example, biomarker system 110 may determine a number of clusters of cancer samples (and their corresponding chromosomal regions) where the regions had distances to the predetermined number of control sample hits (e.g., less than 50%) of at least a predefined or predetermined number of base pairs (e.g., 10s of bps, 100s of bps, 1000s of bps, etc.). A predetermined number (e.g., 32) of cluster regions (e.g., those having less than 50% to no next control sample hits within 200 bp) may be identified to provide a 89% sensitivity with 100% true negative classification, where a sample is called positive if at least one hit is found in any of the cluster regions (see Table 2). In another example, using a higher number of sequences, clusters can be determined where cancer samples show losses, such as those marked by "normal" in table 7.

In one embodiment, biomarker system 100 may further restrict the determined clusters to where only one or less normal sample was found in a cluster region of a given number of cancer samples (e.g., 12). By applying the same rules as above (at least a predefined or predetermined number of base pairs from the next hit), biomarker system 110 may select a predetermined number of these regions (e.g., 37) to yield 94% true positives and 95% true negatives. The total length in one example was calculated to be 667 kbp (see Table 3). Use of 323 regions provides an 87% sensitivity and 100% specificity.

In step 450, one or more clusters of control samples are determined with less than a predetermined number of cancer samples within at least a predefined or predetermined number of base pairs. For example, biomarker system 110 may determine a number of clusters of control samples (and their corresponding chromosomal regions) where the regions had distances to the predetermined number of cancer sample hits (e.g., less than 50%) of at least a predefined or predetermined number of base pairs (e.g., 10s of bps, 100s of bps, 1000s of bps, etc.).

In various aspects, a search for genomic clusters performed by biomarker system 110 over the whole non-repetitive genome can result in a selection of a predetermined number of regions (e.g., clusters) covering a predetermined number of base pairs (e.g., 297kbp) sufficient to give a rate of 93% true positives at a 97% true negative level (see Table 4). Excluding those regions that had one hit in normals, a true positive rate of 88% can be achieved with 100% specificity.

In further embodiments, a further search can be performed by biomarker system 110 for the best cluster combination, where no false positive result was tolerated. Table 5 shows biomarkers 27 clusters with a total length of 257 kbp where the sensitivity was 90% with no false positive detected.

Using a selection of 56 BrCa sera and 35 normals a short sequence tag study was performed. By doing so, the hit count per sample was increased by about II-fold and the same approach as shown above for long sequences was used to define hotspot clusters. By using 23 regions, spanning about 79 kbp, 53156 BrCa patients are correctly classified, which calculates to 95%, when all controls were correctly classified (see Table 6).

In a further attempt, a subset of 143 BrCa samples and 96 Controls were sequenced on a Lifetechnologies SOLiD4+ System. Briefly, samples were prepared as described for the 454 sequencing (0051 &0052), where adaptors specific to SOLiD sequencing are used. For each sample around 5 million reads of 40 bp were achieved and aligned to the Human genome (Build Hg18) using the Lifetechnologies "Bioscope" software suite with default stringency values. All uniquely aligned reads were used for further analysis.

In order to define the chromosomal regions, where samples of either group cluster in comparison to the second group, all hits are ranked in order of their appearance on the chromosomes. Regions were more that 15 hits covering at least 10 samples of a group were found, but not more than one sample of the other group were considered.

Figure 5:
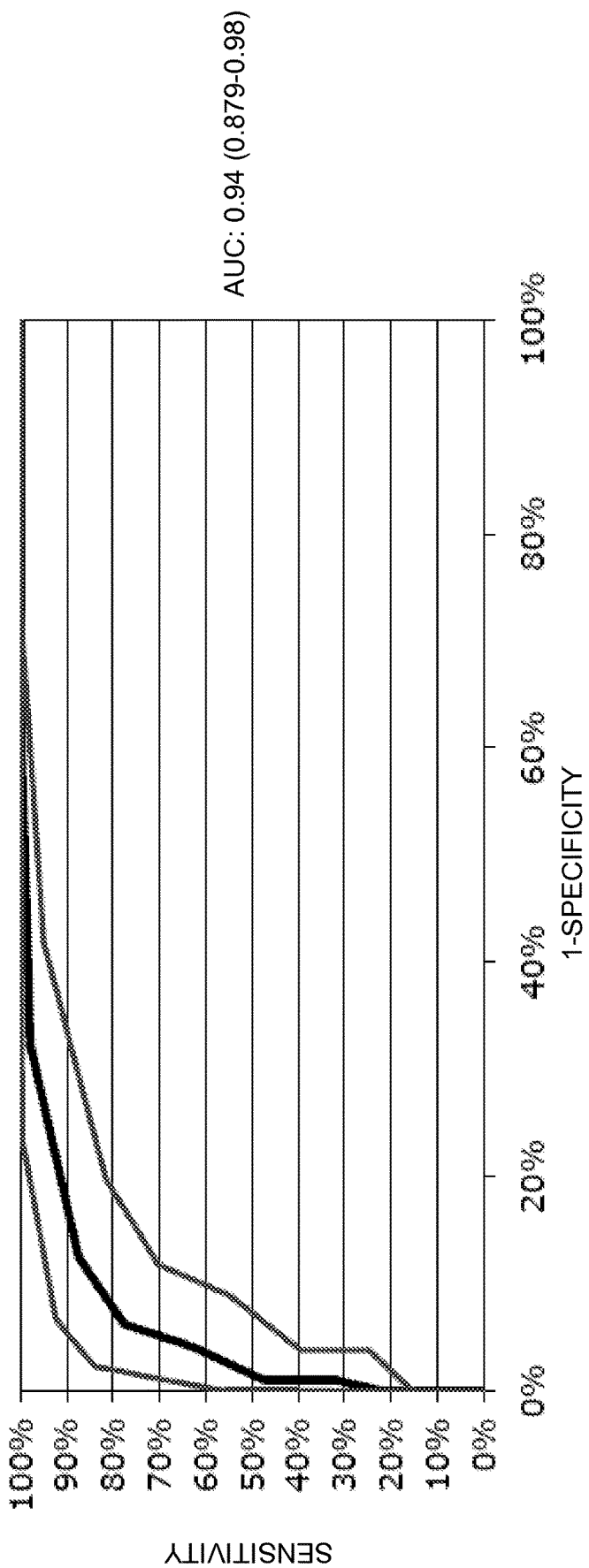
FIG. 5 is a graph illustrating an ROC curve using a set of highest ranking regions in one embodiment according to the present invention.

In 1500 rounds of random resampling the samples are divided into a training and validation set of 50% of each group. For each region, a sample in the region gets a score of 1 if the cluster is a BrCa cluster and a score of −1 for region where normal samples cluster. The average AUC for the validation set was found to be 0.88 if the score sums of 42 cluster regions are used. The regions used in the 1500 round of res amp ling were ranked according to the number of round in which either region participated. Table 7 shows the 56 highest ranking regions. There regions were used in a final calculation on all samples, the ROC curve using the 42 highest ranking regions is shown in FIG. 5.

In further embodiments, methods, systems, kits, and devices of detecting the presence of a biomarker in CNA from a patient that has, or is suspected of having, cancer can be provided. For example, the presence of anyone of the biomarkers listed in Tables 2-7 can be indicative of breast cancer. As appreciated by one of skill in the art, biomarkers may be employed in analyzing a patient sample where the biomarker has also been observed infrequently in a normal patient to in order to increase the sensitivity of the detection. For example, the biomarkers indicated by bold font in Tables 3 and 4 have been observed to be present infrequently in CNA obtained from normal individuals; however, given the low frequency of occurrence in normal samples relative to the higher frequency of occurrence in breast cancer, the presence of the biomarker in a patient indicates that the patient has a 90% or greater likelihood of having breast cancer. Thus, for example, arrays used to detect the chromosomal regions can include those that identify the chromosomal regions in Tables 3 and 4 that are indicated in bold font.

EXAMPLES

Example 1: Identification of breast cancer-associated CNA

Sequencing of CNA—After extraction of DNA from serum or plasma, using standard silica based methods, a whole genome amplification was performed in duplicate. The products were pooled and used for further analysis.

Long sequencing runs—The primer sequences for 454 sequencing were added to the product using fusion primers in not more than 20 cycles of PCR. The resulting product was treated according to the 454 sequencer manual and used for direct sequence detection.

High density short tag runs—The whole genome amplification product was cut with NlaIII endonuclease and ligated to artificial linkers harboring a EcoP15I restriction recognition site. After cutting and re-ligation the resulting linkered di-tags were re-amplified, followed by a NlaIII cut and concatemerization of the linker-free di-tags. Sequencing primers with identifiers are ligated in the same step and the resulting product consisting of up to 20 sequence tags of bout 26 bp in length was subjected to 454 sequencing according to the manufacturers manual.

Computational analysis of sequences with reads longer than 40 bp -The sequence reads were appointed to the sample source by reading the identifier sequence string and all non-source parts were cut out (e.g. primers).

The origin of the circulating DNA was investigated by local alignment analyses using the BLAST program using high stringent parameters. Repetitive elements were detected and masked by using a local install of the Repeatmasker software package using the repbase (version 12.09) that was obtained from the Genetic Information Research Institute. After masking of the repetitive elements and region of low sequence complexity each sequence was subjected to sequential BLAST analyses querying databases of bacterial, viral and fungal genomes and the human genome (reference genome build 37.1). Bacterial, viral, fungal and human genomes were obtained from the National Center for Biotechnology Information (NCBI, (ftp.ncbi.nih.gov)). After each of the sequential database searches all parts of a queried sequence that produced significant hits (e <0.0001) were masked and masked sequences were subsequently used to query the next database. Masked nucleotides were counted and subtracted from the total nucleotide counts resulting in the amounts of unidentified nucleotides.

For each query fragment and each database search, the highest scoring BLAST hit with a length of more than 50% of the query sequence was recorded in a SQL database. The highest scoring BLAST hit was defined as the longest hit with the highest percent identity (maximum of hitlength x identity). For each of the sequences, the start and stop positions for query and database were recorded.

Computational analysis of short sequence tags—after identifying the sample source as given above, the sequences were first dissected at each NlaIII restriction recognition side into ditags. These are cut into tags by using the following algorithm: If ditag-length is even use lengthJ2 bases from the left and right side of ditag to generate tags. If ditag-length is odd use integer(length/2) number of bases from right and left side of ditag to generate tags.

The genomic origin of the tags was investigated by local alignment analyses using the BLAST program using high stringent parameters. Closely comparable result can be achieved using other alignment programs such as BowTie. For each query fragment and each database search, the highest scoring alignment hit with a) no mismatch if tag length is <21 or b) not more than one mismatch if tag length is 21 or higher, and only one such a hit exist, the tag position on the respective genome database as recorded in a SQL database. This short tag method also serves as an example for sequencing that generated short sequence tags per se such as SOLiD™(Applied Biosystems/Life Tech.) or Solexa (Illumina Inc.).

All patents, patent applications, and other published reference materials cited in this specification are hereby incorporated herein by reference in their entirety for their disclosures of the subject matter in whose connection they are cited herein.

Figure 6:
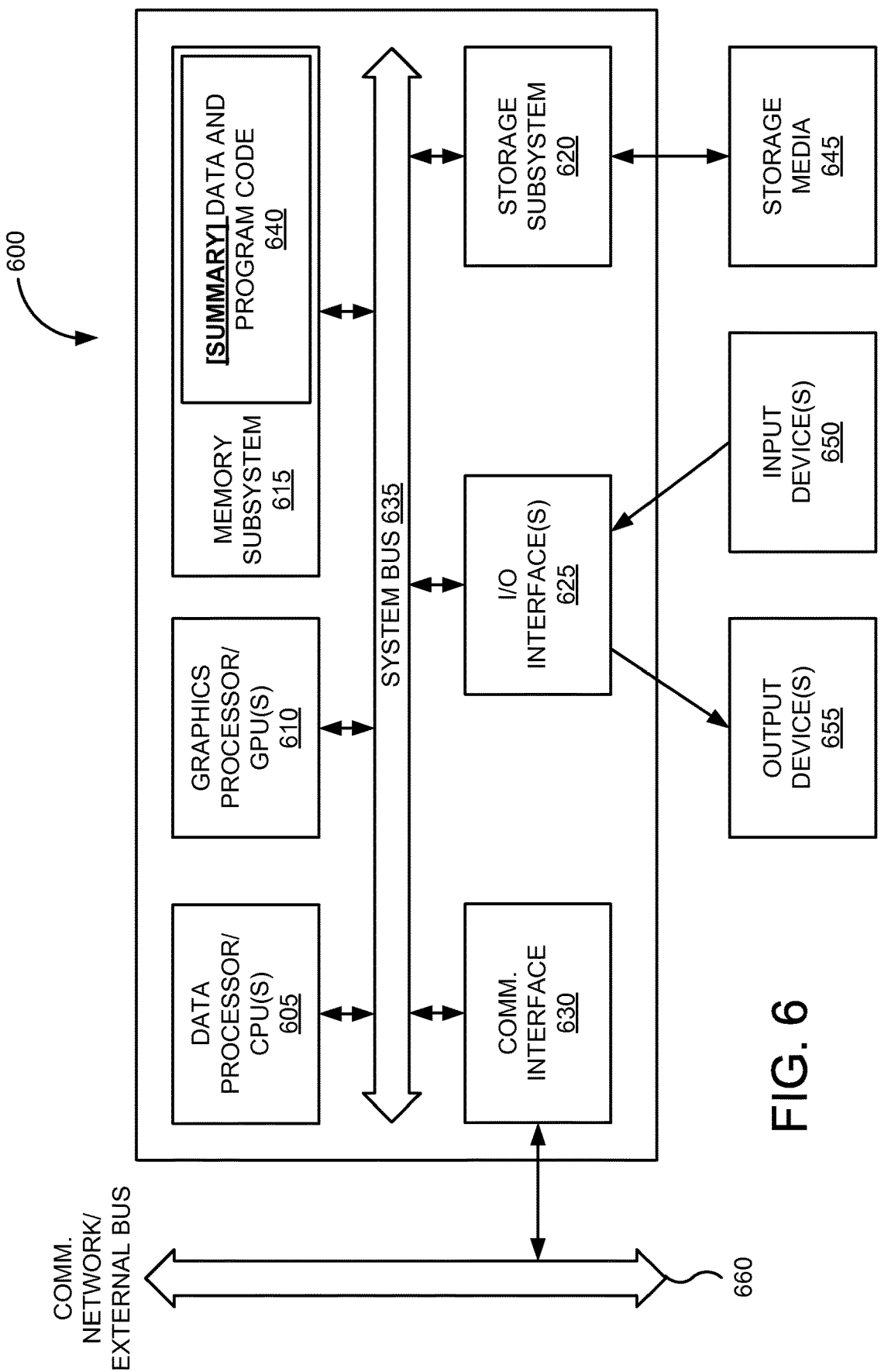
FIG. 6 is a block diagram of a computer system or information processing device that may incorporate an embodiment, be incorporated into an embodiment, or be used to practice any of the innovations, embodiments, and/or examples found within this disclosure.

FIG. 6 is a block diagram of computer system or information processing device 600 that may incorporate an embodiment, be incorporated into an embodiment, or be used to practice any of the innovations, embodiments, and/or examples found within this disclosure. FIG. 6 is merely illustrative of a computing device, general-purpose computer system programmed according to one or more disclosed techniques, or specific information processing device for an embodiment incorporating an invention whose teachings may be presented herein and does not limit the scope of the invention as recited in the claims. One of ordinary skill in the art would recognize other variations, modifications, and alternatives.

Computer system 600 can include hardware and/or software elements configured for performing logic operations and calculations, input/output operations, machine communications, or the like. Computer system 600 may include familiar computer components, such as one or more one or more data processors or central processing units (CPUs) 605, one or more graphics processors or graphical processing units (GPUs) 610, memory subsystem 615, storage subsystem 620, one or more input/output (I/O) interfaces 625, communications interface 630, or the like. Computer system 600 can include system bus 635 interconnecting the above components and providing functionality, such connectivity and inter-device communication. Computer system 600 may be embodied as a computing device, such as a personal computer (PC), a workstation, a mini-computer, a mainframe, a cluster or farm of computing devices, a laptop, a notebook, a netbook, a PDA, a smartphone, a consumer electronic device, a gaming console, or the like.

The one or more data processors or central processing units (CPUs) 605 can include hardware and/or software elements configured for executing logic or program code or for providing application-specific functionality. Some examples of CPU(s) 605 can include one or more microprocessors (e.g., single core and multi-core) or micro-controllers. CPUs 605 may include 4-bit, 8-bit, 12-bit, 16-bit, 32-bit, 64-bit, or the like architectures with similar or divergent internal and external instruction and data designs. CPUs 605 may further include a single core or multiple cores. Commercially available processors may include those provided by Intel of Santa Clara, California (e.g., x86, x86_64, PENTIUM, CELERON, CORE, CORE 2, CORE ix, ITANIUM, XEON, etc.), by Advanced Micro Devices of Sunnyvale, California (e.g., x86, AMD 64, ATHLON, DURON, TURION, ATHLON XP/64, OPTERON, PHENOM, etc.). Commercially available processors may further include those conforming to the Advanced RISC Machine (ARM) architecture (e.g., ARMv7-9), POWER and POWERPC architecture, CELL architecture, and or the like. CPU(s) 605 may also include one or more field-gate programmable arrays (FPGAs), application-specific integrated circuits (ASICs), or other microcontrollers. The one or more data processors or central processing units (CPUs) 605 may include any number of registers, logic units, arithmetic units, caches, memory interfaces, or the like. The one or more data processors or central processing units (CPUs) 605 may further be integrated, irremovably or moveably, into one or more motherboards or daughter boards.

The one or more graphics processor or graphical processing units (GPUs) 610 can include hardware and/or software elements configured for executing logic or program code associated with graphics or for providing graphics-specific functionality. GPUs 610 may include any conventional graphics processing unit, such as those provided by conventional video cards. Some examples of GPUs are commercially available from NVIDIA, ATI, and other vendors. In various embodiments, GPUs 610 may include one or more vector or parallel processing units. These GPUs may be user programmable, and include hardware elements for encoding/decoding specific types of data (e.g., video data) or for accelerating 2D or 3D drawing operations, texturing operations, shading operations, or the like. The one or more graphics processors or graphical processing units (GPUs) 610 may include any number of registers, logic units, arithmetic units, caches, memory interfaces, or the like. The one or more data processors or central processing units (CPUs) 605 may further be integrated, irremovably or moveably, into one or more motherboards or daughter boards that include dedicated video memories, frame buffers, or the like.

Memory subsystem 615 can include hardware and/or software elements configured for storing information. Memory subsystem 615 may store information using machine-readable articles, information storage devices, or computer-readable storage media. Some examples of these articles used by memory subsystem 670 can include random access memories (RAM), read-only-memories (ROMS), volatile memories, non-volatile memories, and other semiconductor memories. In various embodiments, memory subsystem 615 can include CNA analysis data and program code 640.

Storage subsystem 620 can include hardware and/or software elements configured for storing information. Storage subsystem 620 may store information using machine-readable articles, information storage devices, or computer-readable storage media. Storage subsystem 620 may store information using storage media 645. Some examples of storage media 645 used by storage subsystem 620 can include floppy disks, hard disks, optical storage media such as CD-ROMS, DVDs and bar codes, removable storage devices, networked storage devices, or the like. In some embodiments, all or part of CNA analysis data and program code 640 may be stored using storage subsystem 620.

In various embodiments, computer system 600 may include one or more hypervisors or operating systems, such as WINDOWS, WINDOWS NT, WINDOWS XP, VISTA, WINDOWS 7 or the like from Microsoft of Redmond, Washington, Mac OS or Mac OS X from Apple Inc. of Cupertino, California, SOLARIS from Sun Micro systems , LINUX, UNIX, and other UNIX-based or UNIX-like operating systems. Computer system 600 may also include one or more applications configured to executed, perform, or otherwise implement techniques disclosed herein. These applications may be embodied as CNA analysis data and program code 640. Additionally, computer programs, executable computer code, human-readable source code, cluster analysis code, statistical or rules engines, or the like, and data, such as sequence files, models, or the like, may be stored in memory subsystem 615 and/or storage subsystem 620.

The one or more input/output (I/O) interfaces 625 can include hardware and/or software elements configured for performing I/O operations. One or more input devices 650 and/or one or more output devices 655 may be communicatively coupled to the one or more I/O interfaces 625.

The one or more input devices 650 can include hardware and/or software elements configured for receiving information from one or more sources for computer system 600. Some examples of the one or more input devices 650 may include a computer mouse, a trackball, a track pad, a joystick, a wireless remote, a drawing tablet, a voice command system, an eye tracking system, external storage systems, a monitor appropriately configured as a touch screen, a communications interface appropriately configured as a transceiver, or the like. In various embodiments, the one or more input devices 650 may allow a user of computer system 600 to interact with one or more non-graphical or graphical user interfaces to enter a comment, select objects, icons, text, user interface widgets, or other user interface elements that appear on a monitor/display device via a command, a click of a button, or the like.

The one or more output devices 655 can include hardware and/or software elements configured for outputting information to one or more destinations for computer system 600. Some examples of the one or more output devices 655 can include a printer, a fax, a feedback device for a mouse or joystick, external storage systems, a monitor or other display device, a communications interface appropriately configured as a transceiver, or the like. The one or more output devices 655 may allow a user of computer system 600 to view objects, icons, text, user interface widgets, or other user interface elements.

A display device or monitor may be used with computer system 600 and can include hardware and/or software elements configured for displaying information. Some examples include familiar display devices, such as a television monitor, a cathode ray tube (CRT), a liquid crystal display (LCD), or the like.

Communications interface 630 can include hardware and/or software elements configured for performing communications operations, including sending and receiving data. Some examples of communications interface 630 may include a network communications interface, an external bus interface, an Ethernet card, a modem (telephone, satellite, cable, ISDN), (asynchronous) digital subscriber line (DSL) unit, Fire Wire interface, USB interface, or the like. For example, communications interface 630 may be coupled to communications network/external bus 680, such as a computer network, to a FireWire bus, a USB hub, or the like. In other embodiments, communications interface 630 may be physically integrated as hardware on a motherboard or daughter board of computer system 600, may be implemented as a software program, or the like, or may be implemented as a combination thereof.

In various embodiments, computer system 600 may include software that enables communications over a network, such as a local area network or the Internet, using one or more communications protocols, such as the HTTP, TCP/IP, RTP/RTSP protocols, or the like. In some embodiments, other communications software and/or transfer protocols may also be used, for example IPX, UDP or the like, for communicating with hosts over the network or with a device directly connected to computer system 600.

As suggested, FIG. 6 is merely representative of a general-purpose computer system appropriately configured or specific data processing device capable of implementing or incorporating various embodiments of an invention presented within this disclosure. Many other hardware and/or software configurations may be apparent to the skilled artisan, which are suitable for use in implementing an invention presented within this disclosure or with various embodiments of an invention presented within this disclosure. For example, a computer system or data processing device may include desktop, portable, rack-mounted, or tablet configurations. Additionally, a computer system or information processing device may include a series of networked computers or clusters/grids of parallel processing devices. In still other embodiments, a computer system or information processing device may techniques described above as implemented upon a chip or an auxiliary processing board.

Various embodiments of any of one or more inventions whose teachings may be presented within this disclosure can be implemented in the form of logic in software, firmware, hardware, or a combination thereof. The logic may be stored in or on a machine-accessible memory, a machine-readable article, a tangible computer-readable medium, a computer-readable storage medium, or other computer/machine-readable media as a set of instructions adapted to direct a central processing unit (CPU or processor) of a logic machine to perform a set of steps that may be disclosed in various embodiments of an invention presented within this disclosure. The logic may form part of a software program or computer program product as code modules become operational with a processor of a computer system or an information-processing device when executed to perform a method or process in various embodiments of an invention presented within this disclosure. Based on this disclosure and the teachings provided herein, a person of ordinary skill in the art will appreciate other ways, variations, modifications, alternatives, and/or methods for implementing in software, firmware, hardware, or combinations thereof any of the disclosed operations or functionalities of various embodiments of one or more of the presented inventions.

The disclosed examples, implementations, and various embodiments of anyone of those inventions whose teachings may be presented within this disclosure are merely illustrative to convey with reasonable clarity to those skilled in the art the teachings of this disclosure. As these implementations and embodiments may be described with reference to exemplary illustrations or specific figures, various modifications or adaptations of the methods and/or specific structures described can become apparent to those skilled in the art. All such modifications, adaptations, or variations that rely upon this disclosure and these teachings found herein, and through which the teachings have advanced the art, are to be considered within the scope of the one or more inventions whose teachings may be presented within this disclosure. Hence, the present descriptions and drawings should not be considered in a limiting sense, as it is understood that an invention presented within a disclosure is in no way limited to those embodiments specifically illustrated.

Accordingly, the above description and any accompanying drawings, illustrations, and figures are intended to be illustrative but not restrictive. The scope of any invention presented within this disclosure should, therefore, be determined not with simple reference to the above description and those embodiments shown in the figures, but instead should be determined with reference to the pending claims along with their full scope or equivalents.

TABLE 1

| Chromo-some | Region Start position- End position | Cyto banding | Rank (AIC) | Chromo-some length |
|---|---|---|---|---|
| Hs1 | 181500001-182250000 | 1q25.3 | 18 | 226.9 Mb |
|  | 23250001-24000000 | 1p36.11/12 | 24 |  |
|  | 145500001-146250000 | 1q21.1 | 39 |  |

TABLE 1-continued

| Chromo-some | Region Start position- End position | Cyto banding | Rank (AIC) | Chromo-some length |
|---|---|---|---|---|
| Hs2 | 194250001-195000000 | 2q32.3 | 6 | 238.4 Mb |
|  | 219000001-219750000 | 2q35 | 10 |  |
|  | 75000000-75750000 | 2p12/13.1 | 11 |  |
|  | 207750001-208500000 | 2q33.3 | 22 |  |
| Hs4 | 173250001-174000000 | 4q34.1 | 31 | 188.1 Mb |
|  | 38250001-39000000 | 4p14 | 42 |  |
| Hs5 | 9000001-9750000 | 5p15.2 | 2 | 177.7 Mb |
|  | 169500001-170250000 | 5q35.1 | 20 |  |
|  | 60000000-60750000 | 5q12.1 | 30 |  |
| Hs7 | 105750001-106500000 | 7q22.2/3 | 14 | 156 Mb |
|  | 129750001-130500000 | 7q32.2/3 | 15 |  |
|  | 120000001-120750000 | 7q31 | 28 |  |
|  | 75000001-75750000 | 7q11.23 | 41 |  |
| Hs8 | 8250001-9000000 | 8q23.1 | 12 | 143 Mb |
|  | 120000001-120750000 | 8q24.12 | 17 |  |
|  | 123000001-123750000 | 8q24.13 | 36 |  |
| Hs9 | 93750001-94500000 | 9q22.31 | 8 | 121.5 Mb |
|  | 123000001-123750000 | 9q33.2 | 9 |  |
|  | 65250001-66000000 | 9q12 | 29 |  |
| Hs10 | 118500001-119250000 | 10q25.3-26.11 | 4 | 131.7 Mb |
|  | 15000001-15750000 | 10p13 | 21 |  |
|  | 78750001-79500000 | 10q22.3 | 32 |  |
| Hs12 | 11250001-12000000 | 12p13.2 | 33 | 130.5 Mb |
|  | 51750001-52500000 | 12q13.13 | 35 |  |
|  | 14250001-15000000 | 12p13.1-3 | 38 |  |
| Hs13 | 48750001-49500000 | 13q14.2/3 | 13 | 95.6 Mb |
|  | 42000001-42750000 | 13q14.11 | 19 |  |
|  | 60750001-61500000 | 13q21.31 | 25 |  |
|  | 33000001-33750000 | 13q13.2 | 26 |  |
|  | 89250001-90000000 | 13q31.3 | 34 |  |
| Hs14 | 92250001-93000000 | 14q32.12/13 | 16 | 88.3 Mb |
|  | 45000001-45750000 | 14q21.3 | 27 |  |
| Hs15 | 30750001-31500000 | 15q13.3-q14 | 23 | 82.2 Mb |
|  | 58500001-59250000 | 15q22.2 | 40 |  |
| Hs16 | 15000001-15750000 | 16p13.11 | 7 | 78.9 Mb |
| Hs17 | 750001-1500000 | 16p13.3 | 1 | 78.2 Mb |
|  | 53250001-54000000 | 16q12.2 | 5 |  |
| Hs19 | 3750001-4500000 | 16p13.3 | 3 | 56.1 Mb |
|  | 1500001-2250000 | 16p13.3 | 37 |  |

TABLE 2

| Chromo-some | Start Position | End Position | Length | Unique Length | # Ind. | In Table #1 Line # |
|---|---|---|---|---|---|---|
| Hs15 | 58794736 | 58803474 | 8739 | 6434 | 10 | 312 |
| Hs1 | 78991300 | 79003202 | 11903 | 9921 | 9 |  |
| Hs5 | 9729109 | 9741877 | 12769 | 9030 | 10 | 319 |
| Hs15 | 58818514 | 58831712 | 13199 | 8655 | 11 | 3110 |
| Hs1 | 182086265 | 182099422 | 13158 | 8420 | 12 | 315 |
| Hs16 | 15314189 | 15328734 | 14546 | 7256 | 10 | 3112 |
| Hs1 | 23712399 | 23728155 | 15757 | 7362 | 10 | 3114 |
| Hs13 | 42263335 | 42280086 | 16752 | 12651 | 9 |  |
| Hs2 | 75150255 | 75167108 | 16854 | 6889 | 11 | 3115 |
| Hs16 | 15267421 | 15284486 | 17066 | 8241 | 15 | 3117 |
| Hs8 | 8539816 | 8557163 | 17348 | 10469 | 9 |  |
| Hs8 | 120597158 | 120615223 | 18066 | 15444 | 12 | 3118 |
| Hs1 | 146117570 | 146135831 | 18262 | 8667 | 11 | 317 |
| Hs9 | 123059233 | 123077867 | 18635 | 8192 | 10 | 318 |
| Hs16 | 15656188 | 15675324 | 19137 | 5138 | 9 |  |
| Hs10 | 15267696 | 15287050 | 19355 | 10718 | 9 | 3119 |
| Hs1 | 84837904 | 84859107 | 21204 | 15386 | 10 |  |
| Hs13 | 42174182 | 42195708 | 21527 | 12804 | 12 | 3123 |
| Hs17 | 53361889 | 53384434 | 22546 | 14868 | 10 | 3125 |
| Hs9 | 93851754 | 93876478 | 24725 | 12638 | 13 |  |
| Hs4 | 38893729 | 38919556 | 25828 | 14993 | 11 | 3128 |
| Hs16 | 15476486 | 15505558 | 29073 | 11073 | 11 |  |
| Hs4 | 38284097 | 38313299 | 29203 | 10008 | 10 | 3129 |
| Hs18 | 69612722 | 69643198 | 30477 | 15782 | 10 |  |
| Hs5 | 60570005 | 60603234 | 33230 | 22961 | 16 | 3131 |
| Hs19 | 4176228 | 4211314 | 35087 | 12332 | 10 | 3132 |

TABLE 2-continued

| Chromosome | Start Position | End Position | Length | Unique Length | # Ind. | In Table #1 Line # |
|---|---|---|---|---|---|---|
| Hs15 | 58890793 | 58926229 | 35437 | 17261 | 18 | |
| Hs13 | 89372537 | 89409391 | 36855 | 17599 | 9 | |
| Hs2 | 75480588 | 75519417 | 38830 | 10976 | 11 | |
| Hs7 | 75298908 | 75341904 | 42997 | 9795 | 15 | |
| Hs8 | 8304215 | 8351172 | 46958 | 20562 | 15 | |
| Hs1 | 23301973 | 23355587 | 53615 | 12393 | 12 | |

| | | |
|---|---|---|
| # Regions | 32 | |
| # TP | 159 | |
| Sens. | 89.3% | |
| # FP | 0 | |

TABLE 3

| Chromosome | Start Position | End Position | Length | Unique Length | # Ind. | In Table #1 Line # |
|---|---|---|---|---|---|---|
| Hs5 | 9333503 | 9342335 | 8833 | 7802 | 12 | |
| Hs15 | 58794736 | 58803474 | 8739 | 6434 | 10 | 211 |
| Hs7 | 130047281 | 130058242 | 10962 | 8485 | 11 | |
| Hs9 | 65803788 | 65815473 | 11686 | 8868 | 16 | |
| Hs1 | 182086265 | 182099422 | 13158 | 8420 | 12 | 215 |
| Hs7 | 120732445 | 120748893 | 16449 | 13715 | 10 | |
| Hs1 | 146117570 | 146135831 | 18262 | 8667 | 11 | 2113 |
| Hs9 | 123059233 | 123077867 | 18635 | 8192 | 10 | 2114 |
| Hs5 | 9729109 | 9741877 | 12769 | 9030 | 10 | 213 |
| Hs15 | 58818514 | 58831712 | 13199 | 8655 | 11 | 214 |
| Hs13 | 61452626 | 61467317 | 14692 | 9991 | 9 | |
| Hs16 | 15314189 | 15328734 | 14546 | 7256 | 10 | 216 |
| Hs16 | 77305582 | 77320831 | 15250 | 10016 | 9 | |
| Hs1 | 23712399 | 23728155 | 15757 | 7362 | 10 | 217 |
| Hs2 | 75150255 | 75167108 | 16854 | 6889 | 11 | 219 |
| Hs7 | 130398172 | 130415016 | 16845 | 7155 | 9 | |
| Hs16 | 15267421 | 15284486 | 17066 | 8241 | 15 | 2110 |
| Hs8 | 120597158 | 120615223 | 18066 | 15444 | 12 | 2112 |
| Hs10 | 15267696 | 15287050 | 19355 | 10718 | 9 | 2116 |
| Hs7 | 57676796 | 57679502 | 2707 | 1881 | 9 | |
| Hs1 | 181517895 | 181536854 | 18960 | 11299 | 10 | |
| Hs2 | 75699375 | 75718717 | 19343 | 11404 | 12 | |
| Hs13 | 42174182 | 42195708 | 21527 | 12804 | 12 | 2118 |
| Hs4 | 38634946 | 38656586 | 21641 | 9559 | 8 | |
| Hs17 | 53361889 | 53384434 | 22546 | 14868 | 10 | 2119 |
| Hs1 | 181589981 | 181612578 | 22598 | 15064 | 14 | |
| Hs7 | 130423517 | 130447831 | 24315 | 9298 | 9 | |
| Hs4 | 38893729 | 38919556 | 25828 | 14993 | 11 | 2121 |
| Hs4 | 38284097 | 38313299 | 29203 | 10008 | 10 | 2123 |
| Hs12 | 11306311 | 11335781 | 29471 | 19673 | 16 | |
| Hs5 | 60570005 | 60603234 | 33230 | 22961 | 16 | 2125 |
| Hs19 | 4176228 | 4211314 | 35087 | 12732 | 10 | |
| Hs1 | 146145061 | 146161296 | 16236 | 10912 | 13 | |
| Hs2 | 208420571 | 208427991 | 7421 | 4684 | 11 | |
| Hs5 | 9139816 | 9160426 | 20611 | 15318 | 14 | |
| Hs5 | 9416135 | 9437285 | 21151 | 14292 | 8 | |
| Hs8 | 120185767 | 120205636 | 19870 | 9008 | 11 | |

| | | |
|---|---|---|
| # Regions | 37 | 32 |
| # TP | 168 | 155 |
| Sens. | 94.4% | 87.1% |
| # FP | 5 | |
| Spec. | 95.4% | 100% |

TABLE 4

| Chromosome | Start Position | End Position | Length | Unique Length | # Ind. | In Table #1 Line # |
|---|---|---|---|---|---|---|
| Hs1 | 16927708 | 16936899 | 9192 | 5680 | 18 | 5111 |
| Hs22 | 23048139 | 23058946 | 10808 | 7394 | 13 | |
| Hs8 | 134828201 | 134841476 | 13276 | 8948 | 14 | |
| Hs1 | 16892504 | 16901698 | 9195 | 5770 | 13 | 5110 |
| Hs5 | 37802351 | 37812027 | 9677 | 5506 | 11 | 5114 |
| Hs10 | 106523167 | 106534967 | 11801 | 7935 | 12 | |
| Hs5 | 38337804 | 38351003 | 13200 | 8379 | 11 | |
| Hs2 | 121682895 | 121691799 | 8905 | 5988 | 12 | 518 |
| Hs8 | 1001452 | 1011206 | 9755 | 8569 | 11 | |
| Hs11 | 18383367 | 18393825 | 10459 | 5369 | 13 | |
| Hs4 | 82734215 | 82744864 | 10650 | 6248 | 12 | |
| Hs9 | 123940664 | 123951579 | 10916 | 8398 | 11 | 5120 |
| Hs4 | 187267286 | 187278661 | 11376 | 7591 | 11 | |
| Hs8 | 61370490 | 61382562 | 12073 | 6913 | 11 | |
| Hs2 | 15861648 | 15873720 | 12073 | 7806 | 14 | 5123 |
| Hs1 | 156983200 | 156995819 | 12620 | 5427 | 14 | |
| Hs9 | 66744276 | 66749359 | 5084 | 3539 | 11 | 511 |
| Hs14 | 106780499 | 106786136 | 5638 | 3900 | 12 | 512 |
| Hs15 | 92982464 | 92989482 | 7019 | 5084 | 11 | |
| Hs15 | 71935511 | 71943475 | 7965 | 5400 | 11 | |
| Hs2 | 107547731 | 107556647 | 8917 | 6714 | 11 | |
| Hs2 | 1944023 | 1953149 | 9127 | 7379 | 11 | |
| Hs15 | 62540507 | 62549957 | 9451 | 7634 | 11 | 5113 |
| Hs1 | 98947389 | 98957038 | 9650 | 7345 | 11 | 5115 |
| Hs4 | 157820520 | 157831401 | 10882 | 7020 | 11 | |
| Hs2 | 7908924 | 7919887 | 10964 | 7733 | 11 | |
| Hs5 | 154171630 | 154183562 | 11933 | 7656 | 11 | |
| Hs12 | 104286879 | 104296769 | 9891 | 5255 | 11 | |
| Hs1 | 245718410 | 245727864 | 9455 | 6710 | 12 | |
| Hs11 | 120178388 | 120187909 | 9522 | 4629 | 13 | |

| | | |
|---|---|---|
| # Regions | 30 | 27 |
| # TP | 166 | 157 |
| Sens. | 93.3% | 88.2% |
| # FP | 3 | 0 |
| Spec. | 97.2% | 100% |

TABLE 5

| Chromosome | Start Position | End Position | Length | Unique Length | # Ind. | In Table #1 Line # |
|---|---|---|---|---|---|---|
| Hs9 | 66744276 | 66749359 | 5084 | 3539 | 11 | 4117 |
| Hs14 | 106780499 | 106786136 | 5638 | 3900 | 12 | 4118 |
| Hs2 | 168582125 | 168589072 | 6948 | 4841 | 11 | |
| Hs1 | 152507011 | 152514345 | 7335 | 4952 | 11 | |
| Hs2 | 103409691 | 103416973 | 7283 | 3441 | 11 | |
| Hs4 | 187581788 | 187590239 | 8452 | 5505 | 11 | |
| Hs5 | 2303672 | 2312431 | 8760 | 6870 | 12 | |
| Hs2 | 121682895 | 121691799 | 8905 | 5988 | 12 | 418 |
| Hs3 | 8393895 | 8402964 | 9070 | 4971 | 11 | |
| Hs1 | 16892504 | 16901698 | 9195 | 5770 | 13 | 414 |
| Hs1 | 16927708 | 16936899 | 9192 | 5680 | 18 | 411 |
| Hs4 | 31023419 | 31032806 | 9388 | 7983 | 11 | |
| Hs15 | 62540507 | 62549957 | 9451 | 7634 | 11 | 4123 |
| Hs5 | 37802351 | 37812027 | 9677 | 5506 | 11 | 415 |
| Hs1 | 98947389 | 98957038 | 9650 | 7345 | 11 | 4124 |
| Hs18 | 41809704 | 41819480 | 9777 | 7064 | 12 | |
| Hs5 | 6521932 | 6532055 | 10124 | 7081 | 12 | |
| Hs18 | 6856187 | 6866416 | 10230 | 7131 | 11 | |
| Hs11 | 35954290 | 35964889 | 10600 | 6168 | 12 | |
| Hs9 | 123940664 | 123951579 | 10916 | 8398 | 11 | 4112 |
| Hs19 | 34840006 | 34851079 | 11074 | 7186 | 12 | |
| Hs20 | 31428179 | 31440225 | 12047 | 7311 | 11 | |
| Hs2 | 15861648 | 15873720 | 12073 | 7806 | 14 | 4115 |
| Hs3 | 45816265 | 45828522 | 12258 | 6771 | 12 | |
| Hs14 | 62543243 | 62555478 | 12236 | 7688 | 11 | |

TABLE 5-continued

| Chromosome | Start Position | End Position | Length | Unique Length | # Ind. | In Table #1 Line # |
|---|---|---|---|---|---|---|
| Hs10 | 15859116 | 15871760 | 12645 | 6231 | 11 | |
| Hs1 | 227055177 | 227067787 | 12611 | 8536 | 12 | |

| | |
|---|---|
| # Regions | 27 |
| # TP | 161 |
| Sens | 90.4% |
| # FP | 0 |

TABLE 6

| Chromosome | Start Position | End Position | Length | Unique Length | # Ind. |
|---|---|---|---|---|---|
| Hs14 | 49987035 | 50000858 | 13824 | 4915 | 20 |
| Hs1 | 120440890 | 120451513 | 10624 | 3153 | 19 |
| Hs17 | 26267494 | 26272569 | 5076 | 2751 | 19 |
| Hs15 | 29402690 | 29413505 | 10812 | 9234 | 18 |
| Hs5 | 3306716 | 3307102 | 387 | 387 | 17 |
| Hs8 | 142337087 | 142347990 | 10904 | 8145 | 17 |
| Hs11 | 120997333 | 121001541 | 4209 | 3857 | 17 |
| Hs18 | 77058035 | 77064649 | 6615 | 4816 | 17 |
| Hs1 | 173508677 | 173513715 | 5039 | 440 | 16 |
| Hs2 | 209406837 | 209420259 | 13423 | 5537 | 16 |
| Hs6 | 25097428 | 25103462 | 6035 | 2605 | 16 |
| Hs6 | 170477988 | 170480867 | 2880 | 2168 | 16 |
| Hs10 | 113831560 | 113840757 | 9198 | 5521 | 16 |
| Hs15 | 98411055 | 98420737 | 9683 | 5178 | 16 |
| Hs17 | 70072445 | 70073023 | 579 | 579 | 16 |
| Hs20 | 12067861 | 12074879 | 7019 | 4288 | 16 |
| Hs22 | 49837992 | 49843427 | 5436 | 3372 | 16 |
| Hs7 | 24079846 | 24084079 | 4234 | 2954 | 15 |
| Hs20 | 36255517 | 36260170 | 4654 | 3126 | 15 |
| Hs5 | 167308741 | 167313570 | 4830 | 1745 | 15 |
| Hs1 | 10675607 | 10681070 | 5464 | 3480 | 15 |
| Hs22 | 35869939 | 35878394 | 8456 | 4977 | 15 |
| Hs21 | 46129441 | 46139409 | 9969 | 6709 | 15 |
| Hs19 | 13633867 | 13645688 | 11822 | 3924 | 15 |
| Hs13 | 50589706 | 50603142 | 13437 | 10021 | 15 |

| | | |
|---|---|---|
| Top 17 Regions | 121743 | 66946 |
| All 25 Regions | 184609 | 103882 |

| minimal # Hits to count as positive | Sens(all) | Sens(17) |
|---|---|---|
| 1 | 98.2% | 98.2% |
| 2 | 96.4% | 94.6% |
| 3 | 91.1% | 85.7% |
| 4 | 87.5% | 69.6% |
| 5 | 78.6% | 60.7% |

TABLE 7

| Rank | Chromosome | Position | Region | Grouping |
|---|---|---|---|---|
| 1 | Hs3 | 26.3 Mb | 26316904-26317098 | BrCa |
| 2 | Hs5 | 138.5 Mb | 138546637-138546876 | BrCa |
| 3 | Hs5 | 1.9 Mb | 1895609-1895744 | BrCa |
| 4 | Hs10 | 116.9 Mb | 116886669-116886802 | BrCa |
| 5 | Hs13 | 109 Mb | 108983160-108983305 | BrCa |
| 6 | Hs4 | 15.9 Mb | 15922534-15922765 | BrCa |
| 7 | Hs10 | 75.9 Mb | 75892398-75892532 | normal |
| 8 | Hs1 | 21.5 Mb | 21461150-21461398 | BrCa |
| 9 | Hs3 | 10.2 Mb | 10167419-10167564 | normal |
| 10 | Hs3 | 109 Mb | 109045139-109045270 | BrCa |
| 11 | Hs5 | 131.6 Mb | 131556651-131556869 | BrCa |
| 12 | Hs18 | 26 Mb | 26012771-26012898 | normal |
| 13 | Hs12 | 123.6 Mb | 123553236-123553545 | BrCa |
| 14 | Hs14 | 71.2 Mb | 71183079-71183311 | BrCa |
| 15 | Hs3 | 54.2 Mb | 54201491-54201591 | BrCa |
| 16 | Hs6 | 70.3 Mb | 70348510-70348627 | BrCa |
| 17 | Hs17 | 60.4 Mb | 60439625-60439754 | normal |
| 18 | Hs19 | 49.7 Mb | 49663834-49663995 | BrCa |
| 19 | Hs13 | 55.5 Mb | 55470461-55470661 | BrCa |
| 20 | Hs13 | 40.5 Mb | 40513335-40513451 | BrCa |
| 21 | Hs15 | 95.9 Mb | 95868804-95869053 | BrCa |
| 22 | Hs11 | 24.7 Mb | 24655162-24655310 | BrCa |
| 23 | Hs9 | 113.6 Mb | 113608047-113608176 | BrCa |
| 24 | Hs10 | 120.7 Mb | 120651143-120651387 | BrCa |
| 25 | Hs12 | 7.2 Mb | 7205280-7205480 | BrCa |
| 26 | Hs2 | 37.5 Mb | 37500136-37500260 | BrCa |
| 27 | Hs20 | 39.5 Mb | 39516205-39516408 | BrCa |
| 28 | Hs5 | 108.7 Mb | 108742923-108743062 | BrCa |
| 29 | Hs6 | 54.7 Mb | 54736509-54736604 | BrCa |
| 30 | Hs15 | 81.9 Mb | 81851632-81851811 | BrCa |
| 31 | Hs2 | 13.1 Mb | 13103843-13104004 | BrCa |
| 32 | Hs7 | 75.4 Mb | 75395901-75396027 | BrCa |
| 33 | Hs9 | 77.8 Mb | 77788560-77788689 | BrCa |
| 34 | Hs13 | 110.4 Mb | 110359320-110359567 | normal |
| 35 | Hs4 | 186 Mb | 186017668-186017837 | BrCa |
| 36 | Hs12 | 127.5 Mb | 127539423-127539595 | BrCa |
| 37 | Hs5 | 106.9 Mb | 106949296-106949480 | BrCa |
| 38 | Hs4 | 44 Mb | 44016974-44017119 | BrCa |
| 39 | Hs16 | 26.5 Mb | 26462674-26462938 | BrCa |
| 40 | Hs16 | 13.9 Mb | 13939660-13939769 | normal |
| 41 | Hs3 | 4.6 Mb | 4567129-4567322 | BrCa |
| 42 | Hs15 | 32.1 Mb | 32072109-32072293 | BrCa |
| 43 | Hs9 | 4.8 Mb | 4816508-4816623 | BrCa |
| 44 | Hs7 | 3.2 Mb | 3239026-3239202 | BrCa |
| 45 | Hs5 | 149.7 Mb | 149653105-149653309 | BrCa |
| 46 | Hs10 | 131.7 Mb | 131665070-131665215 | BrCa |
| 47 | Hs7 | 12.9 Mb | 12932213-12932446 | BrCa |
| 48 | Hs15 | 66.8 Mb | 66763691-66763868 | BrCa |
| 49 | Hs8 | 120.7 Mb | 120684337-120684476 | BrCa |
| 50 | Hs5 | 121.5 Mb | 121461146-121461216 | BrCa |
| 51 | Hs18 | 71.5 Mb | 71535848-71535989 | normal |
| 52 | Hs4 | 14.2 Mb | 14175097-14175323 | BrCa |
| 53 | Hs8 | 96.9 Mb | 96945650-96945720 | BrCa |
| 54 | Hs9 | 125.2 Mb | 125204413-125204594 | BrCa |
| 55 | Hs1 | 89.2 Mb | 89223352-89223503 | BrCa |
| 56 | Hs10 | 11.3 Mb | 11335204-11335346 | normal |

What is claimed is:

1. A method of analyzing nucleic acid sequences, the method comprising:
   (a) sequencing amplified acellular DNA from a population of cancer patients subsequent to whole genome amplification of DNA extracted from serum or plasma from said population of cancer patients, wherein said sequencing is performed with one or more individual sequence tags for sample identification, and wherein said sequencing generates at least 50,000 sequences per sample;
   (b) electrically receiving sequence information obtained in (a) on a processor describing one or more of the sequenced amplified acellular DNA from the population of cancer patients;
   (c) electrically receiving sequence information on said processor describing one or more DNA sequences from a cancer free control population;
   (d) electrically performing an analysis comparing the information electrically received on the processor in steps (b) and (c) within a finite number of cluster regions of the human genome by aligning sequences within the finite number of cluster regions from said sequenced acellular DNA from the population of cancer patients with one or more sequences from acellular DNA obtained from the cancer free control population; and (e) electrically identifying one or more biomarkers representative of the type of cancer presented by the population of cancer patients by the processor.

2. The method of claim 1, wherein performing the analysis comprises performing a non-parametric median test to determine a plurality of chromosomal regions and ranking the chromosomal regions in response to linear multivariate regression.

3. The method of claim 1, wherein the population of cancer patients has breast cancer, lung cancer, prostate cancer, gastric cancer, brain cancer, cervical cancer, Hodgkin's lymphoma, non-Hodgkin's lymphoma, kidney cancer, leukemia, liver cancer, skin cancer, ovarian cancer, testicular cancer, thyroid cancer, uterine cancer or colorectal cancer.

4. The method of claim 1, wherein sequencing acellular DNA comprises utilizing adaptors.

5. The method of claim 1, wherein after whole genome amplification and before sequencing, the whole genome amplification products are ligated to the sequence tags.

6. The method of claim 1, further comprising masking repetitive elements.

7. The method of claim 1, wherein the filtered portion of the sequences from said acellular DNA corresponds to a chromosomal region on one or more of chromosomes Hs1, Hs2, Hs5, Hs8, Hs11, or Hs12.

8. The method of claim 7, wherein the chromosomal region is selected from the group consisting of Hs1: 146145061-146161296, Hs1:245718410-245727864, Hs2: 208420571-208427991, Hs5:9139816-9160426, Hs5: 9416135-9437285, Hs8:120185767-120205636, Hs11: 120178388-120187909, and Hs12:104286879-104296769.

9. The method of claim 7, wherein the chromosomal region is selected by performing a linear multivariate regression.

10. The method of claim 1, wherein the acellular DNA corresponds to a plurality of base pair intervals of a predetermined size within a portion of the genome.

11. The method of claim 2, wherein performing the analysis further comprises electrically evaluating on the processor the effectiveness of discrimination between the information electrically received in steps (b) and (c) by calculating an information criterion for each cluster.

12. A method of analyzing nucleic acid sequences, the method comprising:
(a) performing whole genome amplification on nucleic acids extracted from serum or plasma of a population of cancer patients;
(b) enzymatically cutting the whole genome amplification product of (a);
(c) ligating sequencing primers comprising identifiers to the enzymatically cleaved product of (b), wherein the resulting product consists of up to 20 sequence tags;
(d) sequencing the products of step (c), thereby generating at least 50,000 sequences per sample;
(e) receiving sequence information on a processor describing the sequenced nucleic acids of (d);
(f) receiving sequence information on said processor describing nucleic acid sequences from a cancer free control population;
(g) performing an analysis comparing the information received on the processor in steps (e) and (f) within a finite number of cluster regions of the human genome by aligning sequences within the finite number of cluster regions from said sequenced acellular nucleic acids from the population of cancer patients with one or more sequences from acellular nucleic acids obtained from the cancer free control population; and
(h) identifying one or more biomarkers in the serum or plasma of the cancer patient by the processor.

13. The method of claim 12, wherein the sequencing in (d) is performed using high-throughput DNA sequencing configured to generate at least 1,000,000 sequences in parallel.

* * * * *